(12) United States Patent
Fukuda

(10) Patent No.: US 6,516,222 B2
(45) Date of Patent: Feb. 4, 2003

(54) APPARATUS FOR DETERMINING DEGREE OF FATIGUE OF HUMAN BODY

(75) Inventor: Yoshinori Fukuda, Akita (JP)

(73) Assignee: Tanita Corporation, Tokyo (JP)

( * ) Notice: Subject to any disclaimer, the term of this patent is extended or adjusted under 35 U.S.C. 154(b) by 25 days.

(21) Appl. No.: 09/753,453

(22) Filed: Jan. 4, 2001

(65) Prior Publication Data

US 2001/0007055 A1 Jul. 5, 2001

(30) Foreign Application Priority Data

Jan. 5, 2000 (JP) ........................................ 2000-000383

(51) Int. Cl.[7] ................................................. A61B 5/05
(52) U.S. Cl. ..................................................... 600/547
(58) Field of Search ......................................... 600/547

(56) References Cited

U.S. PATENT DOCUMENTS

| | | | |
|---|---|---|---|
| 4,008,712 A | | 2/1977 | Nyboer |
| 4,301,879 A | * | 11/1981 | Dubow .......................... 177/5 |
| 4,314,563 A | | 2/1982 | Wheeler |
| 4,694,922 A | * | 9/1987 | Mairot ...................... 177/178 |
| 5,372,141 A | * | 12/1994 | Gallup et al. ............... 600/547 |
| 5,415,176 A | * | 5/1995 | Sato et al. .................. 600/547 |

FOREIGN PATENT DOCUMENTS

| | | | | |
|---|---|---|---|---|
| JP | 2000-023936 | | 1/2000 | |
| WO | WO 9608198 A | * | 3/1996 | ............ A61B/5/05 |
| WO | WO 99/52425 | | 10/1999 | |

\* cited by examiner

*Primary Examiner*—Max F. Hindenburg
*Assistant Examiner*—Pamela Wingood
(74) *Attorney, Agent, or Firm*—McDermott, Will & Emery

(57) ABSTRACT

Disclosed is an apparatus for determining a degree of fatigue of a human body, comprising: two pairs of electrodes; an electric current source; a voltage measuring unit; an arithmetic unit; a storage unit; and a display unit. The two pairs of electrodes are configured to contact with a body of a person under test. The electric current source feeds a measurement current via selected ones of said electrodes. The voltage measuring unit measures a voltage between another selected ones of said electrodes. The storage unit stores a bioelectrical impedance calculated by said arithmetic unit and a reference value. The arithmetic unit calculates the bioelectrical impedance based on the measurement value from said voltage measuring unit and a degree of fatigue of the person under test by comparing the currently measured value of the bioelectrical impedance with the reference value of the bioelectrical impedance stored in the storage unit. The display unit indicates the degree of fatigue of the person under test.

24 Claims, 12 Drawing Sheets

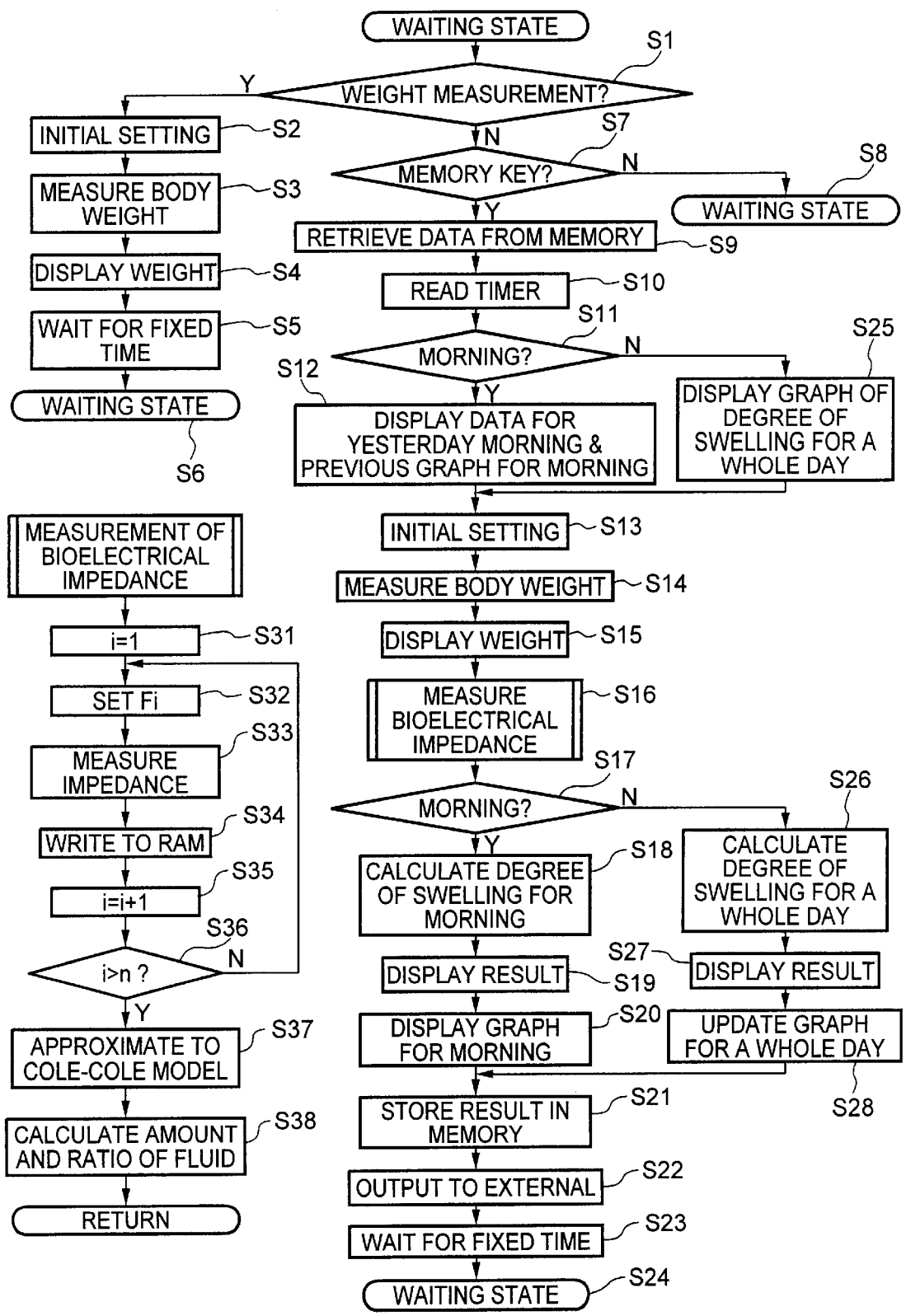

APPARATUS FOR DETERMINING DEGREE OF FATIGUE OF HUMAN BODY

BACKGROUND OF THE INVENTION

1. Field of the Invention

The present invention relates to an apparatus for determining a degree of fatigue of a human body.

2. Description of the Prior Art

In general a swelling can frequently be seen on the leg, and in particular, on the calf of a person when it becomes fatigued in case where the person works while standing for longer period of time, for instance. Such swelling is caused by the reason that a body water or a lymphatic fluid is congested, not smoothly returned to the main body part of the person, under the effect of the gravity. The same swelling can also be seen when the person works while sitting down or the person sits with his legs crossed for longer period of time. In the latter case, bending the legs of the person for longer period of time makes reduced flow of blood and lymphatic fluid at an articulation part of the body, and then, the body water or lymphatic fluid can not smoothly be returned to the main body part. In such manner the swelling can occurs with the fatigue when the person works while keeping the same posture for longer period of time. In any case the gravity is the essential factor that can makes the body water congested. Therefore it can generally be said that the swelling occurs more or less for every person during the time of a day that the person get out of the bed, and the swelling gradually accumulates.

Although the swelling can occur for every person, it is normally restored by the next day. This is due to the fact that the body water becomes spread to the whole body of the person while he is sleeping or lying in the bed.

Such swelling starts to occur at the time the person gets up in the morning and gradually accumulates to reach the maximum at a certain time instance. Such swelling, however, starts to restore after the person goes to bed and is completely restored to substantially same level as that when the person got up in the morning of the previous day. The degree of swelling is changed depending on the activity of the person in a day, and it is not uniform, but different for each of the persons. In addition the sensitivity to the swelling is varies for each of the persons.

Therefore it may happen that in spite of a swelling not restored and a fatigue left accumulated on the next day a person does not feel such swelling so that the he forcibly continues to work, with the result that his health is injured. Alternatively there may be such case where a person feels a swelling on his leg, but he takes an optimistic view of restoration of the swelling on the next day, with the result that he loses sight of a symptom of a critical disease.

In order to obviate such possibility it is preferred to have an apparatus for objectively determining a degree of fatigue of a person. Unfortunately none of such apparatus has been available in the prior art.

SUMMARY OF THE INVENTION

In view of the above it is an object of the present invention is to provide an apparatus for simply determining a degree of fatigue of each of persons.

In order to attain such object the present invention provides an apparatus for determining a degree of fatigue of a human body, comprising: two pairs of electrodes; an electric current source; a voltage measuring unit; an arithmetic unit; a storage unit; and a display unit, whereby said two pairs of electrodes are configured to contact with a body of a person under test;

said electric current source feeds a measurement current via selected ones of said electrodes;

said voltage measuring unit measures a voltage between another selected ones of said electrodes;

said storage unit stores a bioelectrical impedance calculated by said arithmetic unit and a reference value;

said arithmetic unit calculates the bioelectrical impedance based on the measurement value from said voltage measuring unit and a degree of fatigue of the person under test by comparing the currently measured value of the bioelectrical impedance with the reference value of the bioelectrical impedance stored in the storage unit; and said display unit indicates the degree of fatigue of the person under test.

According to one embodiment of the present invention, said display unit graphically indicates the transition of change in degree of fatigue.

According to another embodiment of the present invention, the graph displayed on said display unit represents the transition of change in degree of fatigue on the basis of the bioelectrical impedance as measured in the morning.

According to further embodiment of the present invention, the graph displayed on said display unit represents the transition of change in degree of fatigue on the basis of the bioelectrical impedance as measured in the evening or night.

According to yet further embodiment of the present invention, said reference value of bioelectrical impedance is set before a certain action is carried out by a person under test, and said display unit indicates the degree of fatigue before and after such action by comparing the currently measured value of the bioelectrical impedance with the reference value of the bioelectrical impedance stored in the storage unit.

According to another aspect of the present invention, there is provided an apparatus for determining a degree of fatigue based on the swelling of a human body, comprising: two pairs of electrodes; an electric current source; a voltage measuring unit; an arithmetic unit; a storage unit; and a display unit, whereby said two pairs of electrodes are configured to contact with a body of a person under test;

said electric current source feeds a measurement current via selected ones of said electrodes;

said voltage measuring unit measures a voltage between another selected ones of said electrodes;

said storage unit stores a bioelectrical impedance calculated by said arithmetic unit and a reference value;

said arithmetic unit calculates the bioelectrical impedance based on the measurement value from said voltage measuring unit and a degree of swelling of the person under test by comparing the currently measured value of the bioelectrical impedance with the reference value of the bioelectrical impedance stored in the storage unit; and said display unit indicates a degree of swelling of the person under test.

According to one embodiment of the present invention, said display unit graphically indicates the transition of change in degree of swelling.

According to another embodiment of the present invention, the graph displayed on said display unit represents the transition of change in degree of swelling on the basis of the bioelectrical impedance as measured in the morning.

According to further embodiment of the present invention, the graph displayed on said display unit represents the transition of change in degree of swelling on the basis of the bioelectrical impedance as measured in the evening or night.

According to yet further embodiment of the present invention, said reference value of bioelectrical impedance is set before a certain action is carried out by a person under test, and said display unit indicates the degree of swelling before and after such action by comparing the currently measured value of the bioelectrical impedance with the reference value of the bioelectrical impedance stored in the storage unit.

According to yet further embodiment of the present invention, said reference value of the bioelectrical impedance represents an average change in amount of interstitial fluid that is the difference between average values for a plurality of measurements in every morning and in every night.

According to yet further embodiment of the present invention, said average change in amount of interstitial fluid is updated every time when the bioelectrical impedance is measured.

According to yet further embodiment of the present invention, said electric current source selectively feeds the measurement current having a plurality of frequencies.

According to yet further embodiment of the present invention, said electric current source feeds the measurement current having a single frequency.

According to yet further embodiment of the present invention, said two pairs of electrodes are configured to contact with both soles of the person under test.

According to yet further embodiment of the present invention, said two pairs of electrodes are configured to contact with a calf of the person under test.

BRIEF DESCRIPTION OF THE DRAWINGS

Now the present invention will be described in more detail with reference to the accompanying drawings, in which:

FIG. 10 is a flow chart illustrating the measuring steps in the apparatus for determining the degree of fatigue in FIG. 5;

DESCRIPTION OF THE PREFERRED EMBODIMENTS

Figure 1:
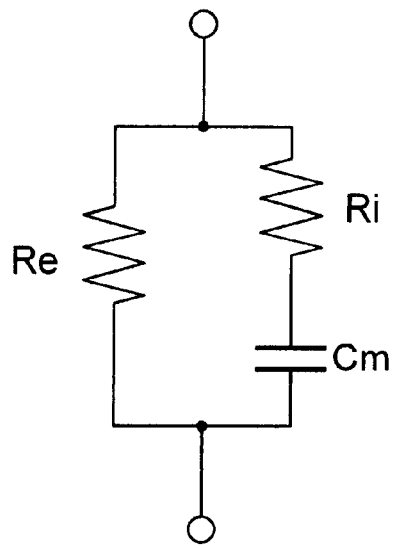
FIG. 1 is a view representing an electrically equivalent circuit of a cell in a tissue of a human body.

First the principle of the present invention will be described. According to the present invention a bioelectrical impedance is measured to detect a degree of swelling that results from the change in distribution of body water in a body of a person in response to his activity in every day. Then a degree of the swelling at that time and the tendency of the swelling over longer period of time are examined so that a degree of fatigue of the body is determined accordingly. Because of the difference in swelling inherently present for each of the persons, as already described, it is not possible to determine the degree of swelling simply by comparing with a fixed reference value. Therefore it is preferred that the standard level for the swelling of the person is measured and stored as the reference in advance. Then, on the basis of such standard level, the degree of swelling at that time and the tendency of the swelling over longer period of time are determined.

Because the exercise and the work of the person that is the living activity after the person gets up is one of the causes for the swelling the fatigue resulting from such living activity can be correlated with the degree of the swelling. Therefore the degree of swelling previously derived can be used for determining the degree of fatigue which is then displayed.

According to the present invention the degree of swelling periodically occurred on a person in the daily life is detected, and it is compared to the reference value for the person. The reference value is derived from the measurement data over a certain time interval because of the fluctuation in degree of swelling inherently present in the person. Then the degree of swelling of the person can objectively be determined.

In addition on the basis of the measurements over a certain interval the condition of the body and the accumulation of fatigue during that interval can objectively be estimated to some degree. Now, an example case is considered where the measurement of swelling is performed at the time a person gets up in the morning and at the time he goes to bed or at a certain time instance in the night over a certain time interval. Thereafter a change in degree of swelling therefor is examined. As described earlier the swelling is normally restored until the time the person gets up in the next morning. However it may happen that the swelling is not completely restored, but the degree thereof gradually accumulates every time when the measurement is performed at the time a person gets up or he goes to bed or at a certain time instance in the night. In such case it is considered that the swelling is not restored within the living cycle of a day, but it gradually accumulates. In other words the fatigue that is not restored within the living cycle of a day has accumulated.

Then the method of measuring a bioelectrical impedance used in the present invention will be described. At first, reference will be made to a multi-frequency bioelectrical impedance measurement method using a plurality of frequencies. According to such measurement method, not only the bioelectrical impedance, but also an amount of body water, an amount of intra-cellular and extra-cellular water in the whole body as well as an amount of water, intra-cellular and extra-cellular water in a measured part of the body can be derived on the basis of a various living body parameters, intra-cellular and extra-cellular water resistance as well as cell membrane capacitance.

An electrical impedance of a living body is typically represented by a lumped constant equivalent circuit comprising an extra-cellular water resistance Re, an intra-cellular water resistance Ri, and a cell membrane capacitance Cm, as shown in FIG. 1. Practically, plural cells making up the living body are respectively represented by individual circuits having different constants due to their different shapes and characteristics. Thus, in the living body as an aggregation of such cells, its vector impedance locus does not show a half circle at variance with the case of measuring the lumped constant equivalent circuit, but shows a circular arc given in the Cole—Cole model.

Figure 2:
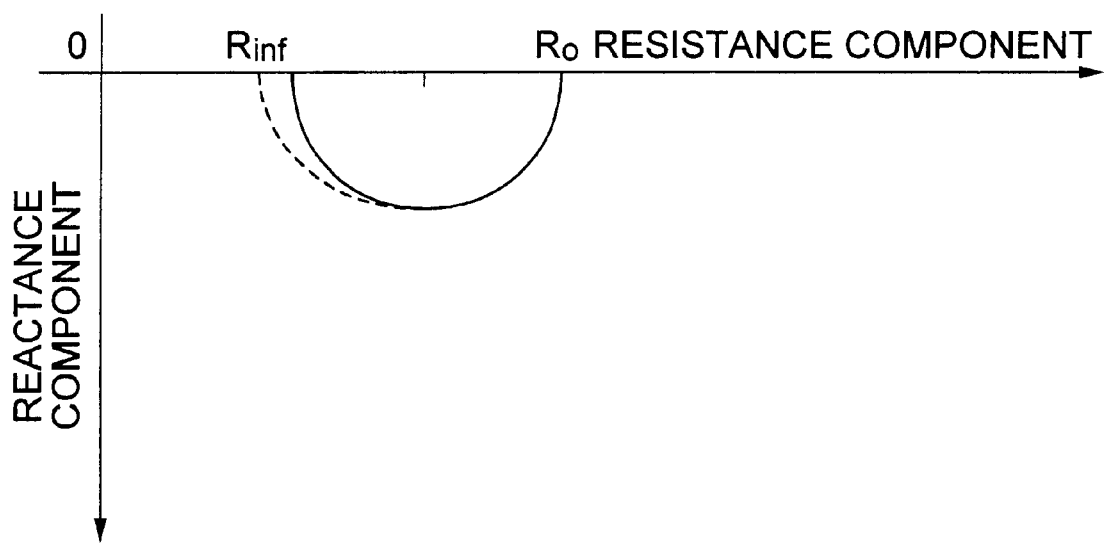
FIG. 2 is a graphical representation of a bioelectrical vector impedance locus of a human body for explaining a bioelectrical impedance measurement used in the present invention.

Thus, the electrical impedance of the living body is generally represented by a circular arc-like locus shown in FIG. 2. In FIG. 2, x-axis represents a resistance component of the impedance, while y-axis represents a reactance component of the impedance. Since the reactance component of the bioelectrical impedance shows a negative value due to its capacitive property, the vector locus of the bioelectrical impedance is plotted on the underside of the real axis as shown in FIG. 2.

Figure 3:
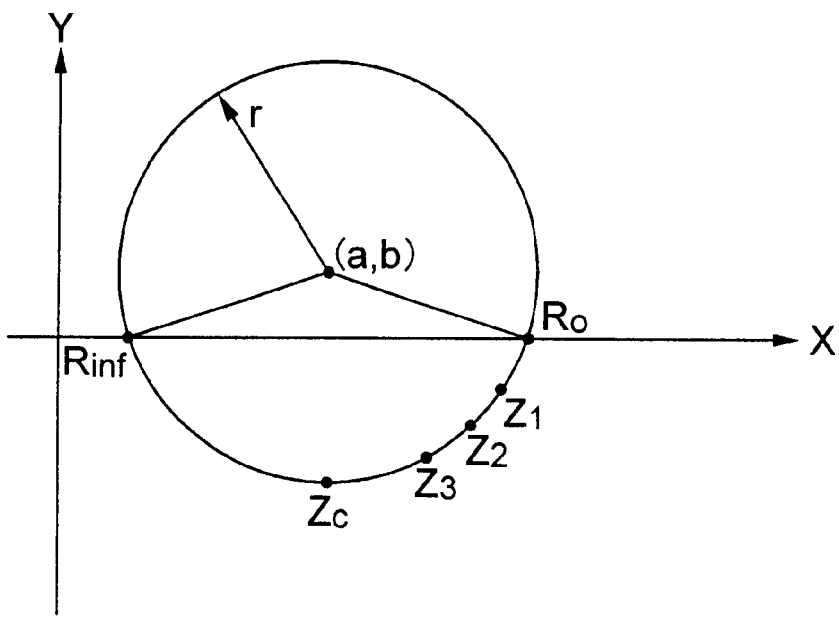
FIG. 3 is a graphical representation illustrating a relation between a point of characteristic frequency and points of zero and infinite frequencies.

Referring to FIG. 3, Ro, Rinf, and Zc respectively indicate a resistance at 0 frequency, a resistance at infinite frequency and a bioelectrical impedance value at frequency Fc. As to Ro and Rinf, they have only a resistance component because their reactance value is zero. At the frequency Fc, an absolute value of the reactance component reaches its maximum, and Zc is a bioelectrical impedance value at this frequency. As used herein, the frequency where the absolute value of the reactance component reaches its maximum is referred to as a characteristic frequency. Each body composition, such as a body water, an intra-cellular water, an extra-cellular water, a fat-free mass and a ratio of intra-cellular to extra-cellular water, is derived from the above values or approximate values thereof.

The swelling is considered as the condition in which too much interstitial fluid (or body water among the cellular texture outside the blood vessel) is collected in a specific area. Alternatively it may be said that too much extra-cellular water is collected in view of the fact that the interstitial fluid is one component of the extra-cellular water. At the same time it may also be said that the body water is increased in view of the fact that the extra-cellular water is one component of the body water. As described earlier, however, the swelling periodically occurred in the daily life is mainly caused by the effect of the gravity, and therefore, the swelling mainly occurs in an area adjacent the extreme parts of the limbs that are far away from the heart. Accordingly an increase in amount of the interstitial fluid or the extra-cellular water or the body water can be produced only in the part of the body where the swelling occurs.

Then reference will be made to a single-frequency bioelectrical impedance measurement method using an AC measurement current having a single frequency. According to such single-frequency bioelectrical impedance measurement method the measured value of the bioelectrical impedance can be used in the same manner as above to estimate an amount of body water between the measured parts of the body. A change in amount of the body water substantially depends on a change in amount of the extra-cellular water. Therefore capturing the change in amount of the body water is equivalent to capturing the change in amount of the extra-cellular water. As already described the change in amount of the interstitial fluid appears as the change in amount of the extra-cellular water. Then it is possible to keep track of the change in degree of the swelling even with the single-frequency bioelectrical impedance measurement method. The method of estimating an amount of body water using an AC current of a single frequency is already known in the art, and therefore, further description of such method is omitted here.

Figures 4A, 4B:
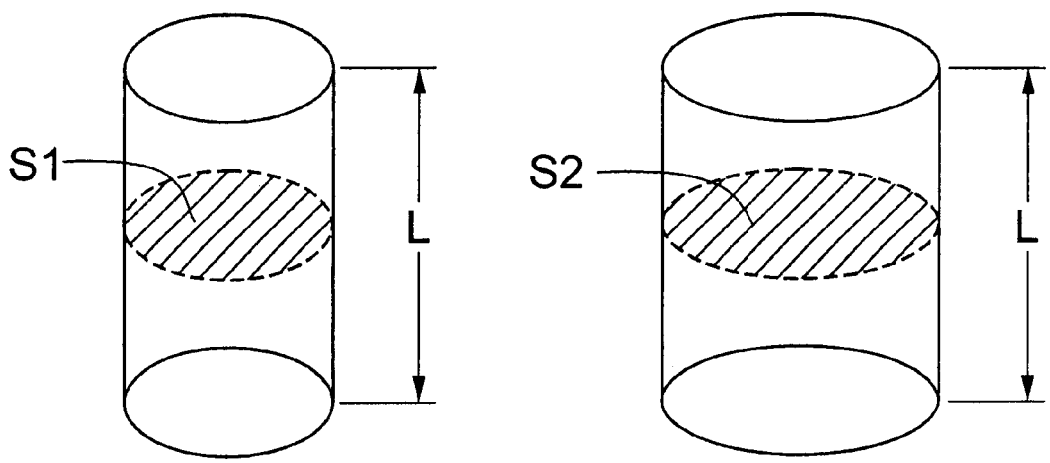
FIGS. 4 (a) and 4(b) are a model illustrating a change in swelling in a human body.

Now, for the purpose of illustration, an amount of interstitial fluid in a certain part of the living body before the swelling occurs is represented by "W1". The interstitial fluid before the swelling occurs is represented in the form of a cylinder having the length "L" and the cross sectional area "S1" as shown in FIG. 4 ($a$). Furthermore the resistivity of the interstitial fluid is represented by "ρ". Then the resistance R1 between both ends of the interstitial fluid is expressed by the following formula:

$$R1 = \rho \cdot L / S1$$

Then it is assumed that the amount of the interstitial fluid is changed to "W2" due to the occurrence of the swelling. At this time the contour of the cylinder of the interstitial fluid is changed so that only the cross sectional area is changed from "S1" to "S2", but the length "L" is held constant, as shown in FIG. 4 ($b$). Then the resistance R2 between both ends of the interstitial fluid is expressed by the following formula:

$$R2 = \rho \cdot L / S2$$

Because of the constant length "L" of the cylinder the amount of the interstitial fluid has proportional relation to the cross sectional area of the cylinder. Therefore "W1" and "W2" are expressed using "R1" and "R2" in the following manner:

$$W1 = k/R1 \tag{1}$$

$$W2 = k/R2 \tag{2}$$

wherein "k" is a constant. Then a change in amount of the interstitial fluid ΔW is expressed by the following formula:

$$\Delta W = W2 - W1$$

Substitution of the formulae (1) and (2) creates the following formula:

$$\Delta W = k/R2 - k/R1$$

$$= k \cdot (R1 - R2)/(R2 \cdot R1)$$

As the result the change in amount of the interstitial fluid can be derived from the measurement of the resistance of the interstitial fluid. In addition, because the change in amount of the interstitial fluid is correlated to the change in amount of the extra-cellular water and the body water in the measured part of the body, as described earlier, the change in amount of the interstitial fluid may be derived from the measurement of the interstitial fluid resistance and the bioelectrical impedance.

In this manner the change in amount of the interstitial fluid is derived. However this simply indicates the quantitative change of the interstitial fluid, but does not indicate the degree of the swelling that has been caused thereby. The relation between the amount of the interstitial fluid and the degree of the swelling varies for each of persons, and can not uniformly be determined on account of different physical feature, different physical constitution, different activity in the daily life and the like.

Therefore, according to the present invention, a personal data for a person is derived by the measurement in normal living circumstances for the person over a certain time interval in advance, and on the basis of the personal data, a reference value for the person is derived. Then a change in amount of the interstitial fluid measured or a resultant data derived therefrom is compared to the reference value for the person to determine the degree of swelling. In this manner the average data for the person can be used for the reference to precisely determine the degree of swelling, the degree of fatigue and the body condition for the person.

Figure 5:
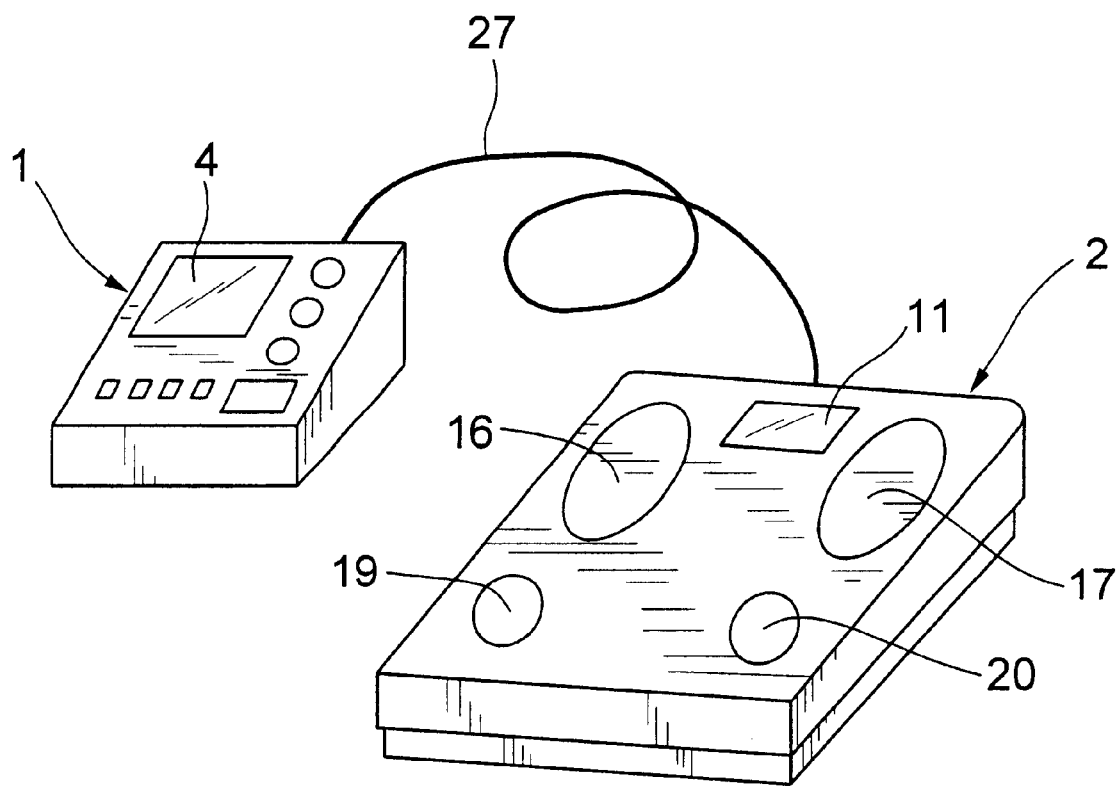
FIG. 5 is an external overview illustrating an apparatus for determining a degree of fatigue of a human body according to one embodiment of the present invention.
Figure 6:
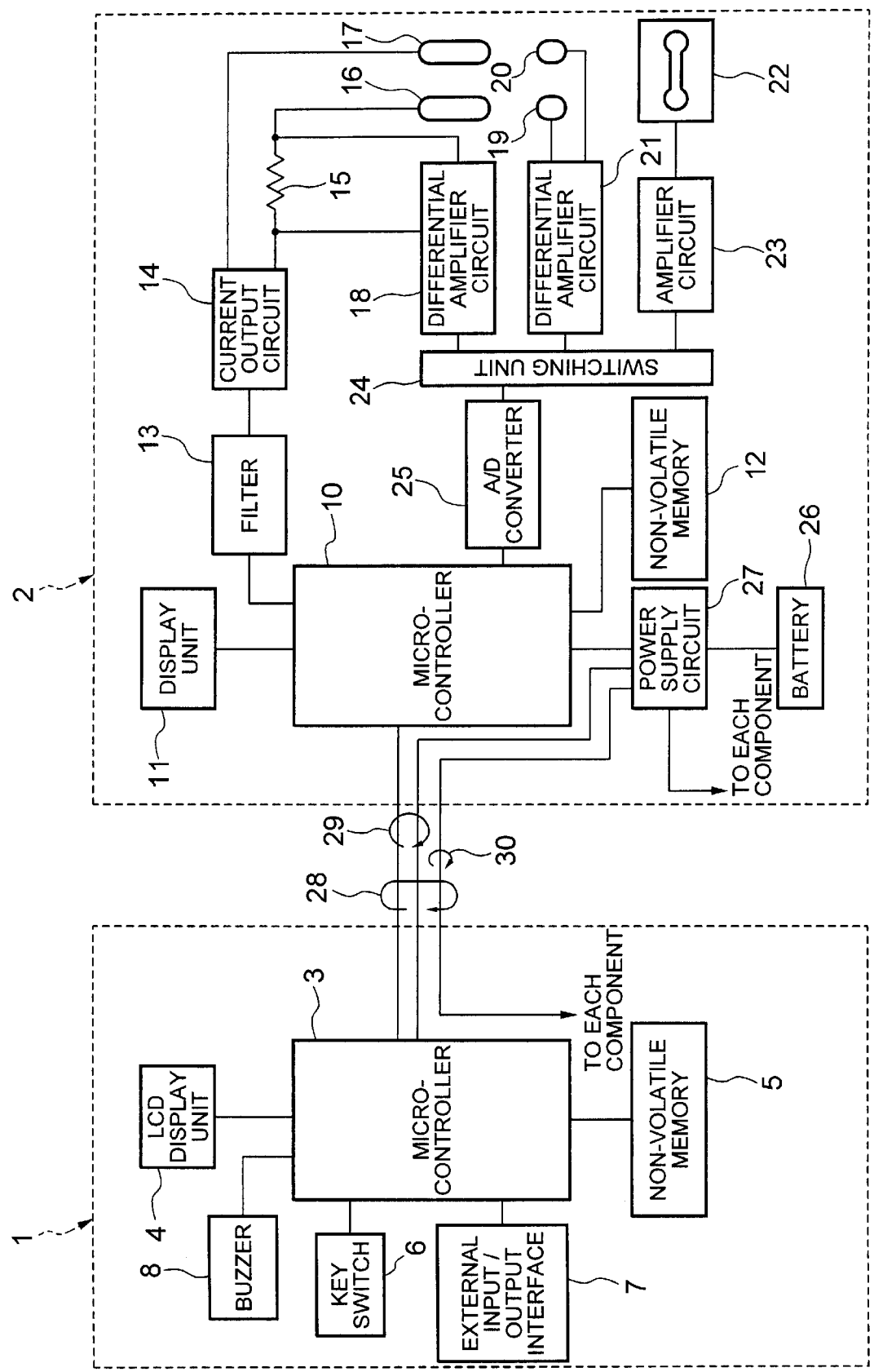
FIG. 6 is a block diagram illustrating principal components of the apparatus for determining the degree of fatigue in FIG. 5.

FIG. 5 is a schematic overview illustrating an apparatus for determining a degree of fatigue for a human body according to one embodiment of the present invention. FIG. 6 is a block diagram illustrating all essential components within the apparatus in FIG. 5. The apparatus for determining the degree of fatigue for the human body according to this embodiment comprises two main units: a controller box 1 and a measuring instrument 2, as shown in FIG. 5. The essential functions in the controller box 1 and the measuring instrument 2 will be described with reference to the block diagram in FIG. 6.

The controller box 1 comprises a micro-controller 3 including a CPU, a ROM, a RAM, a timer, an I/O port and other functions. The controller box 1 further comprises an LCD display unit 4 for displaying personal parameters set by a person under test, a resultant data of the measurement, and a progress of the measurement steps, and a non-volatile memory 5 for storing the measurement control parameters and the personal parameters. The controller box 1 additionally comprises a key switch 6 for entering the personal parameters and for selecting the personal parameters stored in the non-volatile memory 5, and an external input/output interface 7 for communication with the external part. Furthermore a buzzer circuit 8 under the control of the micro-controller 3 is included in the controller box 1.

The measuring instrument 2 comprises a micro-controller 10 including a CPU, a ROM, a RAM, a timer, an I/O port and other functions, and an indicator unit 11 for indicating the progress of measurement steps and the like. The measuring instrument 2 further comprises a non-volatile memory 12 for storing the parameters inherent for the measuring instrument used in the measurement, and a filter circuit 13 for shaping the output signal from the micro-controller 10 into a signal applied to the living body. Also included in the measuring instrument 2 is an AC current output circuit 14 for feeding the output signal from the filter circuit 13 to a person under test. A reference resistor 15 is connected to one of the output terminals of the AC current output circuit 14 for detecting the current to the person under test. A measurement current feeding electrode 16 is connected via the reference resistor 15, and another measurement current feeding electrode 17 is connected to another output terminal of the AC current output circuit 14. A differential amplifier 18 is included for detecting the voltage difference between both terminals of the reference resistor 15. Voltage measurement electrodes 19 and 20 are provided for detecting an electric potential between two points on the person under test. A differential amplifier 21 is connected to the voltage measurement electrodes 19 and 20 for detecting the electric potential therebetween. A weight sensor 22 is provided for detecting the body weight of the person under test, and the weight sensor 22 is connected to an amplifier 23 for amplifying a signal therefrom. A switching unit 24 is operated under the control of the micro-controller 10 for selectively connecting either one of the outputs from the differential amplifiers 18, 21 and the amplifier 23. The output of the switching unit 24 is connected to an A/D converter 25 for converting an analogue signal from the switching unit 24 into a digital signal which is then fed to the micro-controller 10. A battery 26 is contained in the measuring instrument 2 and is connected to a power supply circuit 27. The power supply circuit 27 is operated under the control of the micro-controller 3 of the controller box 1 and the micro-controller 10 of the measuring instrument 2 for supplying an electric power to the components as described above within the controller box 1 and the measuring instrument 2.

The controller box 1 and the measuring instrument 2 are connected to each other via a connection cable 28. The connection cable 28 consists of a plurality of signal lines 29 for communication and a plurality of power lines 30 for supplying electric power between the controller box 1 and the measuring instrument 2.

The signal lines 29 are used for feeding control signals from the micro-controller 3 to the micro-controller 10 and the power supply circuit 27 in order to control the operation and the power supply of the measuring instrument 2. In addition the signal lines 29 sends the measurement result produced in the measuring instrument 2 to the micro-controller 3.

Figure 7:
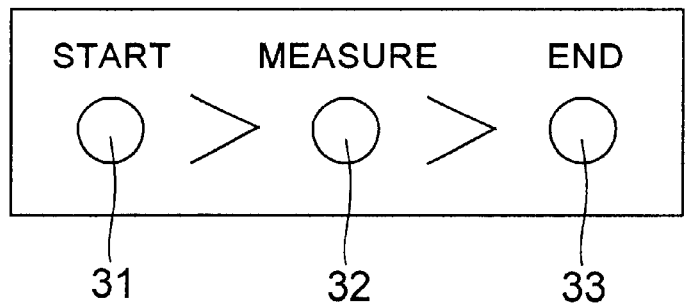
FIG. 7 is an enlarged view illustrating a measuring instrument display unit of the apparatus for determining the degree of fatigue in FIG. 5.

Now the measuring instrument 2 will be described in detail. FIG. 7 is a view illustrating in more detail the display unit 11 of the measuring instrument 2 in FIG. 5. As shown in FIG. 7 the display unit 11 of the measuring instrument 2 includes a first LED 31, a second LED 32 and a third LED 33 which are respectively turned ON to indicate the progress of the measurement process.

The first LED 31 is turned ON after completion of the initial setting of the measuring instrument 2 in order to indicate that the measurement can be started. The first LED 31 is turned OFF after the measurement is started. The second LED 32 is turned ON as soon as the measurement is started, and is held ON during the time that the measurement is over and the arithmetic operation for the measurement result is conducted. The second LED 32 is turned OFF immediately before the arithmetic result is displayed on the controller box 1. The third LED 33 is turned ON after the second LED 32 is turned OFF to indicate that the measurement and the arithmetic operation are finished. The third LED 33 is turned OFF after a fixed time period.

Figure 8:
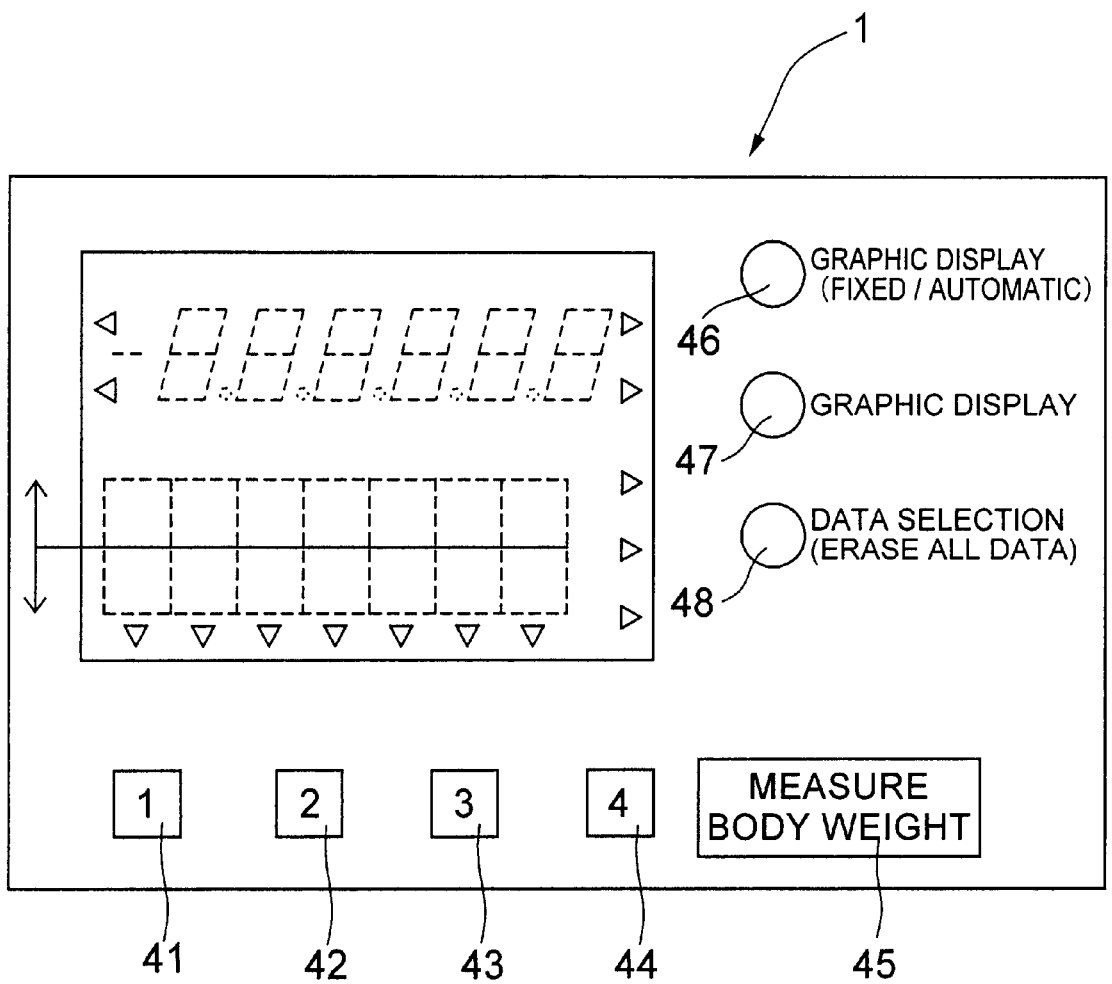
FIG. 8 is an elevation view illustrating a controller box of the apparatus for determining the degree of fatigue in FIG. 5.
Figure 9:
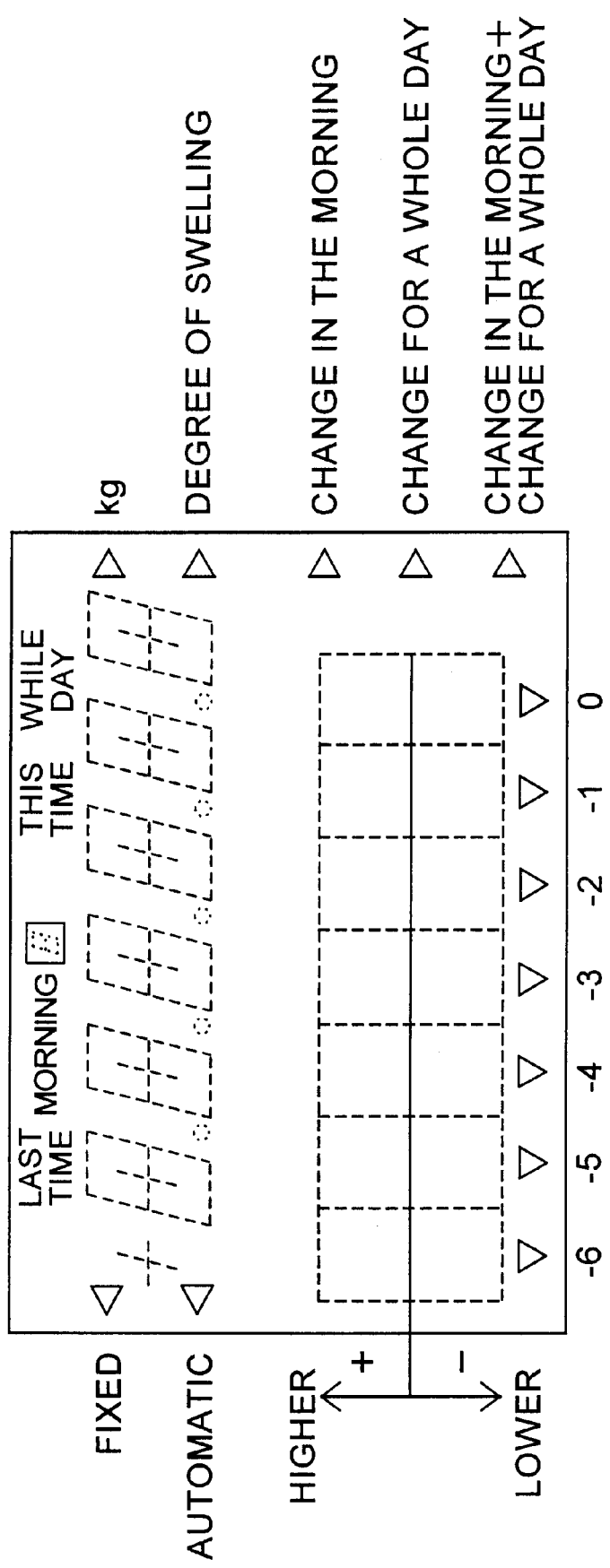
FIG. 9 is an enlarged view illustrating main elements of an LCD display unit of the apparatus for determining the degree of fatigue in FIG. 5.

Next the controller box 1 will be described in more detail. FIGS. 8 and 9 show an operation and display section of the controller box 1. As shown in FIG. 8 the controller box 1 includes an LCD display unit 4 for displaying the measurement result and the previous measurement data, and memory keys 41, 42, 43 and 44 for setting the personal data and for retrieving and correcting the data. The controller box 1 further includes a weight measurement key 45 for conducting the weight measurement rather than the measurement of the degree of swelling, and a graphic display key 46 for turning ON and OFF the display of the previous personal data. In addition a graph selection key 47 for switching between three types of graphs produced in the present apparatus, and a data selection key 48 for selecting the numerical data in the graph displayed for representation thereof are provided in the controller box 1. FIG. 9 is an enlarged view showing the principal elements of the LCD display unit 4.

Now, procedure of measuring operations, retrieval of graphic functions, setting of the personal data as the reference, and calculation of the degree of swelling will be described hereafter. At first the procedure of measuring operations in normal measuring process will be described with reference to a flow chart of FIG. 10. It is assumed, here, that all the personal data representing the personal reference required for arithmetic operation has been set. Although the detailed description will be made latter, it is suffice to say, here, that the personal data is set by an average value "Zam" for bioelectrical impedance as measured in every morning over a certain time interval and an average time "Tam" for measurement time instances at which the measurements are made; as well as an average value "Zpm" for bioelectrical impedance as measured in every evening or night over the same interval and an average time "Tpm" for measurement time instances at which the measurements are made.

Initially upon depressing either one of the memory keys 41, 42, 43, 44 and the weight measurement key 45 the procedure enters an operation mode from a wait mode. At first a check is made to see whether the key depressed is the weight measurement key 45 or not (step S1). If so, the apparatus is operated as the weight meter, and after completion of internal initial setting, the first LED 31 of the display unit 11 on the measuring instrument is turned ON to indicate that the measurement can be started (step S2). When the person under test mounts on the measuring instrument 2 the first LED 31 is turned OFF, but the second LED 32 is turned ON to indicate that the measurement is now performed. When the weight sensor 22 detects the body weight the signal is fed to and amplified by the amplifier 23, of which output signal is then fed to the switching unit 24. Then the signal is fed to the A/D converter 25 that converts it into the digital signal, which signal is fed to the micro-controller 10. Then the micro-controller 10 performs the arithmetic operation to produce the weight value (step S3). After completion of the measurement the second LED 32 is turned OFF, but the third LED 33 is turned ON to indicate that the measurement is finished. At the same time the measurement result is displayed on the LCD display unit 4 (step S4), and after waiting for a fixed time period (step S5), the third LED 33 is turned OFF. Then the measurement data on the LCD display unit 4 is erased and the procedure enters a wait mode (step S6).

If the key depressed is not the weight measurement key 45 in step S1 then a check is made to see whether the key depressed is either one of the memory keys 41, 42, 43 and 44 (step S7). If none of the memory keys is depressed the procedure does not enter an operation mode, but enters a wait mode (step S8).

If either one of the memory keys 41, 42, 43 and 44 is depressed the subsequent operation of the apparatus depends on the time instance when it is depressed. The operation of the apparatus will be described hereafter for two cases: one is that the key is depressed in the morning, and the other is that the key is depressed in the evening. 1. Measurement operation in the morning:

If either one of the memory keys 41, 42, 43 and 44 is depressed in step S7 the data corresponding to the key number of the memory key depressed is read from the non-volatile memory 5 (step S9). In addition the time data when the key is depressed is read from the timer in the micro-controller 3 (step S10). The time data from the timer is compared to a measurement-time-reference for determining whether the measurement is going to perform in the morning, in the evening or in the night. In step S11 a check is made to see whether it is the measurement in the morning or not. Then the weight value as measured in the morning last time and the memory key number are displayed, and the previous data of the degree of swelling in the morning as calculated from the previous data in the morning stored in the non-volatile memory 5 is graphically displayed (step S12). Thereafter the measuring apparatus is initialized (step S13). After the initialization is completed and the measurement operation is ready the first LED 31 is turned ON to indicate that the measurement may be started. When the person under test mounts on the measuring instrument 2 the first LED 31 is turned OFF, but the second LED 32 is turned ON to indicate that the measurement is now performed. When the weight sensor 22 detects the body weight of the person the signal is fed to and amplified by the amplifier 23, of which output signal is then fed to the switching unit 24. Then the signal is fed to the A/D converter 25 that converts it into the digital signal, which signal is fed to the micro-controller 10. Then the micro-controller 10 performs the arithmetic operation to produce the weight value (step S14). This weight value is then displayed on the LCD display unit 4 (step S15). Next the measurement of bioelectrical impedance is performed (step S16). The arithmetic operation is carried out using the personal data as the reference. The measurement of bioelectrical impedance will be described latter. After completion of a sequence of measurement steps the second LED 32 is turned OFF, but the third LED 33 is turned ON to indicate that the measurement is finished. At this point a check is made again to see whether it is the measurement in the morning or not (step S17). If so, the arithmetic operation is carried out to calculate the degree of swelling in the morning (step S18). The degree of swelling in the morning thus calculated is displayed on a numerical display area of the LCD display unit 4, together with the degree of swelling in the morning derived last time and stored in the non-volatile memory 5 (step S19). Then the graph as updated using the data at that time is displayed on a graphic area of the LCD display unit 4 (step S20), and the measurement result at that time and the corresponding measurement time are stored in the non-volatile memory 5 (step S21). If required the measurement result is output via the external input/output interface 7 (step S22), and after waiting for a fixed time period, the third LED 33 is turned OFF and the data on the LCD display unit 4 is erased (step S23). Then the procedure enters a waiting mode (step S24).

2. Measuring operation in the evening or night:

If either one of the memory keys 41, 42, 43 and 44 is depressed in step S7 the data corresponding to the key number of the memory key depressed is read from the non-volatile memory 5 (step S9). In addition the time data when the key is depressed is read from the timer in the micro-controller 3 (step S10). The time data from the timer is compared to the measurement-time-reference for determining whether the measurement is going to perform in the morning, in the evening or in the night. In step S11 a check is made to determine that the measurement is going to perform in the evening or in the night. Then the weight value as measured in the evening or night last time and the corresponding memory key number is displayed. In addition, the degree of swelling in a day as calculated from the previous data in the morning and in the evening or night stored in the non-volatile memory 5 is graphically displayed (step S25). Thereafter the measuring apparatus is initialized (step S13). After the initialization is completed and the measurement operation is ready the first LED 31 is turned ON to indicate that the measurement may be started. When the person under test mounts on the measuring instrument 2 the first LED 31 is turned OFF, but the second LED 32 is turned ON to indicate that the measurement is now performed. When the weight sensor 22 detects the body weight of the person the signal is fed to and amplified by the amplifier 23, of which output signal is then fed to the switching unit 24. Then the signal is fed to the A/D converter 25 that converts it into the digital signal, which signal is fed to the micro-controller 10. Then the micro-controller 10 performs the arithmetic operation to produce the weight value (step S14). This weight value is then displayed on the LCD display unit 4 (step S15). Next the measurement of bioelectrical impedance is performed (step S16). The arithmetic operation is carried out using the personal data as the reference. After completion of a sequence of measurement steps the second LED 32 is turned OFF, but the third LED 33 is turned ON to indicate that the measurement is finished. At this point a check is made again to see whether it is the measurement in the morning or not (step S17). Because of the measurement in the evening or night at this time, the arithmetic operation is performed to calculate the degree of swelling in a day (step S26). Then the degree of swelling in a day thus calculated and the degree of swelling in the morning previously measured are displayed as the measurement result on the numerical area of the LCD display unit 4 (step S27). In addition the graph as updated using the current data is displayed on the graphic area of the LCD display unit 4 (step S28), and the measurement result currently obtained and the corresponding measurement time are stored in the non-volatile memory 5 (step S21). If required the measurement result is output via the external input/output interface 7 (step S22), and after waiting for a fixed time period, the third LED 33 is turned OFF and the data on the LCD display unit 4 is erased (step S23). Then the procedure enters a waiting mode (step S24).

Now the multi-frequency bioelectrical impedance measurement method using an AC current having a plurality of frequencies will be described.

The multi-frequency bioelectrical impedance measurement is performed in such manner that the measurement is repeated "n" times at the frequency Fi wherein "n" can arbitrarily be set and the frequency Fi begins at "i"=1. For the initial setting for the measurement at the first frequency the value of "i" is set to 1 (step S31). Depending on the value of "i" the frequency Fi is set (step S32). On the basis of the measurement control parameters preliminary stored in the ROM of the micro-controller 3 or those stored in the RAM via the external input/output interface 7, the micro-controller 10 sets the frequency of the output signal which is then fed to the current output circuit 14. The current output circuit 14 consists of a constant current output circuit that can set the current value. Therefore the output current is set depending on the measurement control parameters and then it is applied to the person under test via the measurement current supplying electrodes 16 and 17.

Then the electric current applied to the person is detected through the reference resistor 15 and the detected signal in analogue form is fed to the A/D converter 25 that converts it into digital signal which is then stored in the RAM of the micro-controller 10. At the same time an electric potential is detected between the electric potential measurement electrodes 19 and 20 attached to the person and it is fed to the differential amplifier circuit 21. The differential amplifier circuit 21 outputs the potential difference signal that is the difference between the electric potential signals fed thereto to the A/D converter 25. The A/D converter 25 converts such input signal in analogue form into the signal in digital form, which means that the bioelectrical impedance has been measured (step S33). Then the measurement result is stored in the RAM (step S34).

After completion of the impedance measurement at the first frequency the value of "i" is set to "i+1" (step S35) and a check is made to see whether the predetermined number of times for the measurement is reached (step S36). If the value of "i" exceeds the predetermined number of times "n" the impedance measurement goes to end, but if not, the procedure returns to step S32 so that the impedance measurement is repeated at the next frequency.

Thereafter the impedance locus and the corresponding parameter are calculated based on the measured value of bioelectrical impedance. From the reason as described earlier the electrical impedance of the living body is such that its vector impedance locus does not show a half circle, but shows a circular arc given in the Cole-Cole model. Thus, the electrical impedance of the living body is generally represented by a circular arc-like locus shown in FIG. 2. According to an assumption that the vector impedance locus derived is a circular arc, the bioelectrical impedance values Z1, Z2, . . . Zn measured respectively at the frequencies "Fi" (i=1 to n) are on a circular arc of a certain circle as shown in FIG. 3. Herein, a real axis (axis of abscissa) and an imaginary axis (axis of ordinate) of the vector impedance plane are referred to as an X-axis and a Y-axis respectively. Therefore, from the points "Zi" (i=1 to n) on the coordinate, the following correlation function is derived:

$$(X-a)^2+(Y-b)^2=r^2$$

where "a" is X coordinate of the center of the circle, "b" is Y coordinate of the center of the circle, and "r" is a radius of the circle. In other words this function is an approximated correlation function between "n" points. Thus the following formula is derived:

$$X=a\pm\sqrt{(r^2-b^2)}$$

wherein, since Ro>Rinf, $$Ro=a+\sqrt{(r^2-b^2)}$$

$$Rinf=a-\sqrt{(r^2-b^2)}$$

Accordingly, Re and Ri of the equivalent circuit of FIG. 1 are expressed as follows:

$$Re=Ro$$

$$Ri=Ro\cdot Rinf/(R_o-Rinf)$$

The impedance vector Zc at the characteristic frequency Fc is defined as a point where the reactance or the imaginary axis component, that is, the absolute value of Y-axis component, reaches the maximum value. Therefore, X coordinate as a real axis component and Y coordinate as an imaginary axis component of the impedance vector Zc are determined as:

$$X=a,\ Y=b-r$$

and thereby the impedance vector Zc is represented as:

$$Zc=a+j(b-r)$$

According to Cole—Cole model as described earlier the impedance vector at a frequency ω is represented as:

$$Z(\omega) = Rinf + (Ro - Rinf) / (1 + (j\omega\tau)^\beta)$$

where $Z(\omega)$ is the impedance vector at $\omega$, and $\tau$ and $\beta$ are constants.

When $\tau = 1/\omega c$, $$Z(\omega) = Rinf + (Ro - Rinf)/(1 + (j\omega/\omega c)^\beta)$$

where $\omega c = 2\pi Fc$.

Fc and $\beta$ can be calculated also based on these relations and a data on the circle (step S37).

Then, based on the vector impedance locus and the associated parameters thus calculated, such as Ro, Rinf, Re, Ri, Zc and Fc, the amount of extra-cellular water (ECW), the amount of the intra-cellular water (ICW), a ratio of the intra-cellular to extra-cellular water, and the total body water (TBW) are calculated (step S38).

Figure 11A:
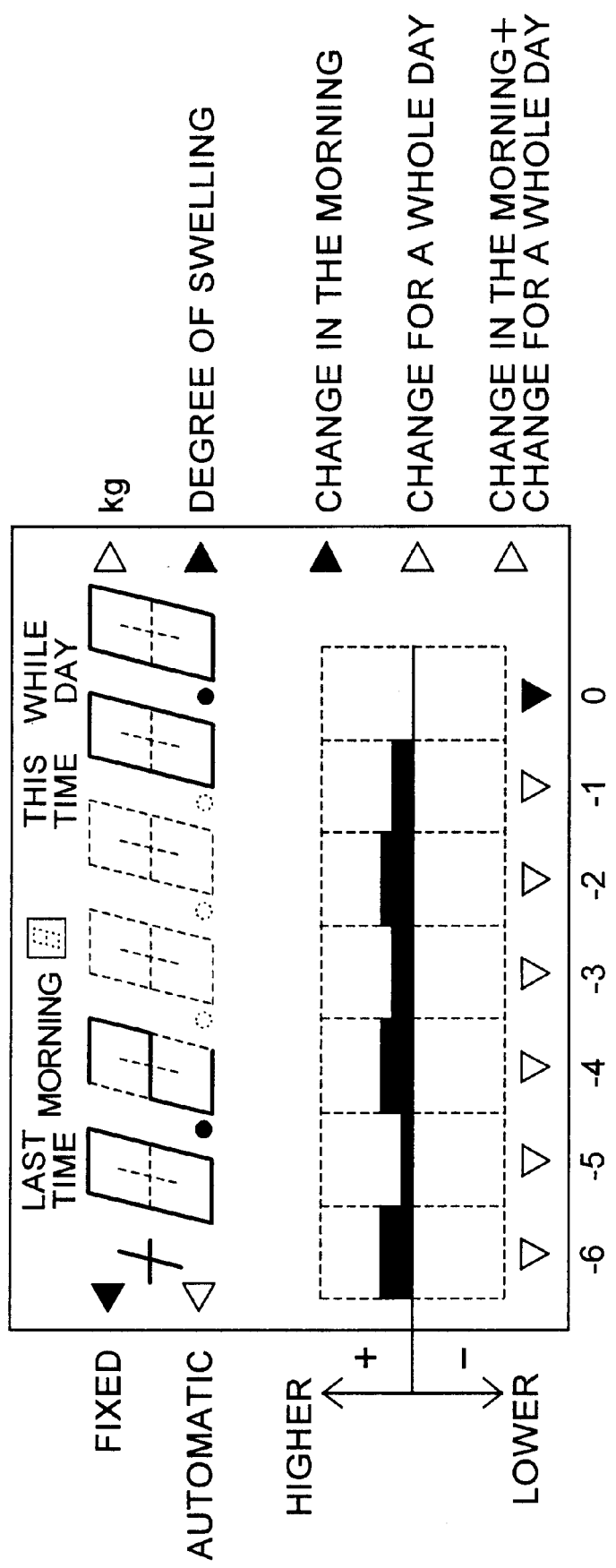
FIGS. 11(a), 11(b) and 11(c) are a view illustrating the LCD display unit on which different types of data are displayed, by way of an example.
Figure 11B:
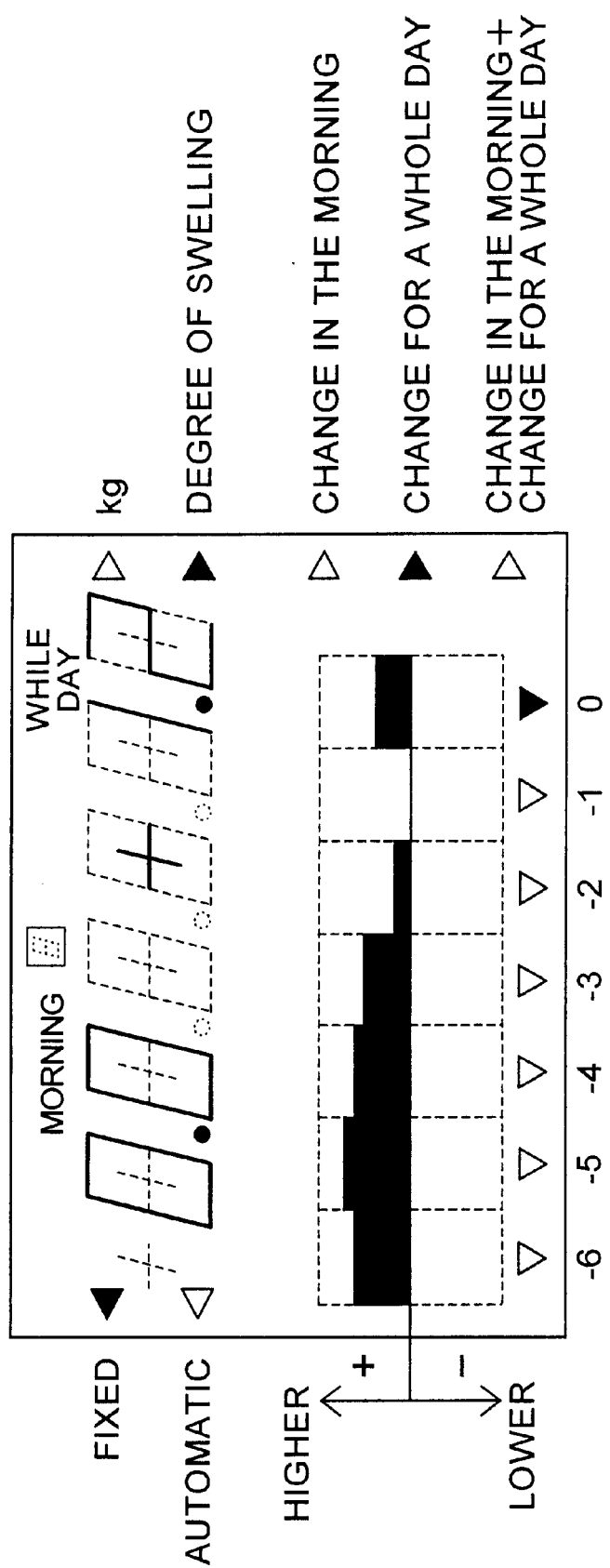
Figure 11C:
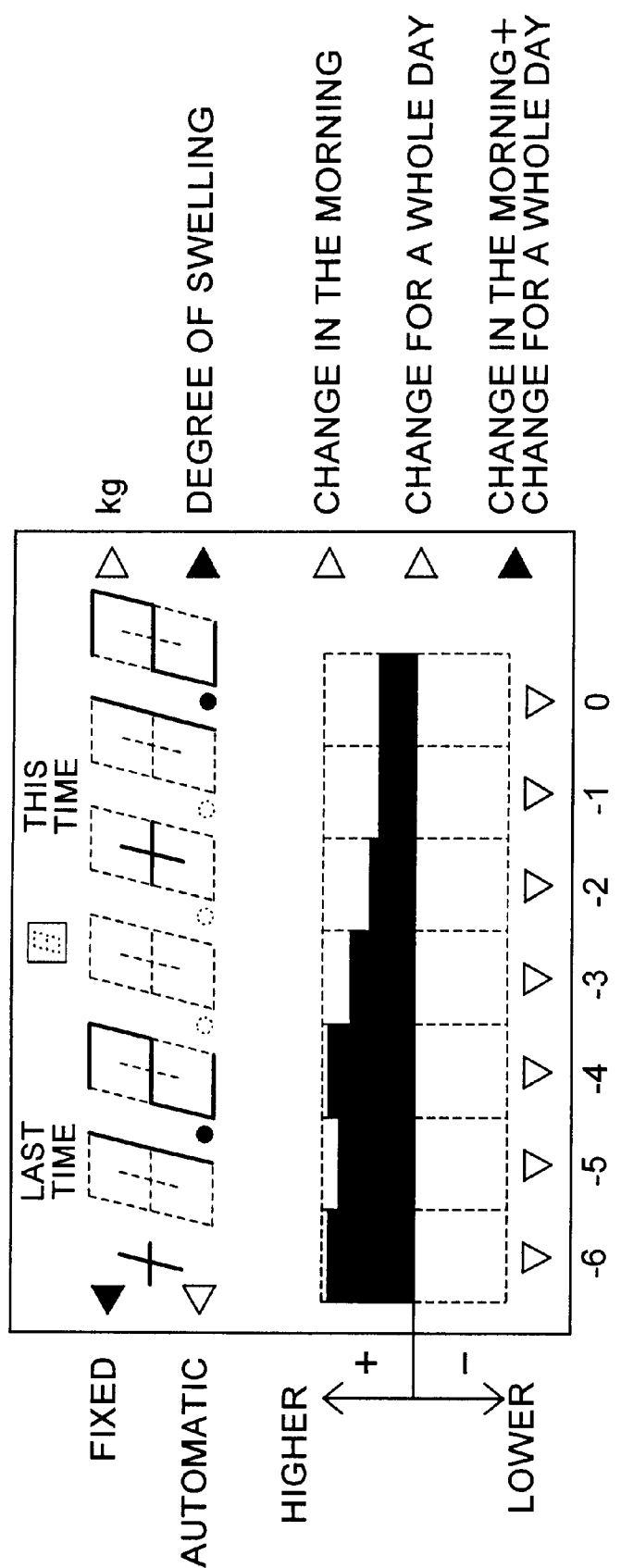

Now the graphic display function will be described with reference to FIGS. 8, 11(a), 11(b) and 11(c). FIGS. 11(a), 11(b) and 11(c) show what is displayed on the LCD display unit 4, by way of an example. The graphic display function starts by depressing the graphic display key 46. Even when the apparatus is in waiting mode depressing the graphic display key 46 puts the apparatus into operation mode to start the graphic display function. However, during the time the apparatus is in the course of measurement process, the graphic display function can not be activated. The operation of the apparatus after the graphic display function is started is hereafter referred to as "graphic mode" of operation.

In the graphic mode when either one of the memory number keys 41, 42, 43 and 44 is depressed the data corresponding to the memory number key depressed is read out from the non-volatile memory 5, processed and displayed. The graph showing the degree of swelling is displayed on the lower portion of the LCD display unit 4 and the numerical data selected is displayed on the upper portion of the LCD display.

FIGS. 11(a), 11(b) and 11(c) show the LCD display unit 4 on which the data stored in the memory No. 1 is displayed, by way of an example. In particular, referring to FIG. 11(a), the LCD display unit graphically represents the data for the morning. In FIG. 11(b) the LCD display unit graphically represents the data for a whole day. In FIG. 11(c) the LCD display unit graphically represents the sum of both data.

Referring to FIG. 11(a), a change in degree of swelling in the morning calculated using the personal data as the reference is represented. More particularly the degree of swelling of +0.2% relative to the reference in the yesterday morning has been changed to 0.0% in this morning.

Referring to FIG. 11(b), a change in degree of swelling for a whole day from the morning to the evening is represented. In particular the degree of swelling of 0.0% in the morning has been changed to +1.2% after completion of the activity in that day.

Referring to FIG. 11(c), a total change in degree of swelling produced by a sum of the degree of swelling for the morning and that for a while day is represented. In particular the degree of swelling was +1.2% relative to the reference for the previous day and it is also +1.2% for that day.

Depressing the graph selection key 47 in succession switches the data display formats (a), (b) and (c) in turn so that one of them appears on the LCD display. In addition depressing the data selection key 48 moves the position of a triangle mark provided under the graph and at the same time the numerical data corresponding to that position of the triangle mark is displayed in the upper portion of the LCD display. Depressing the graph display key 46 once again terminates the graph mode of operation.

Now the personal data serving as the reference will be described. In the embodiment as disclosed herein there are two types of setting mode for setting the personal data serving as the reference (hereafter referred to as "reference data"). One of them is a "fixed setting mode" in which the reference data, once set on the basis of the data over a certain time interval, is continuously used until the time it is to be re-set. The other is an "automatic setting mode" in which the reference data is automatically updated based on the previous data for a certain time interval.

Switching between those setting modes is performed by depressing one of the memory keys 41, 42, 43 and 44 for more than a certain period of time. Then it becomes possible to switch the setting mode in correspondence to the memory key depressed so that not only switching between the fixed mode and the automatic mode, but also erasing of personal measurement data can be done. In association therewith the LCD display unit 4 displays a triangle mark at upper left position thereof that indicates the current setting mode of "fixed" or "automatic". At the same time the memory number and the graph are displayed on the LCD display unit 4. Then depressing the graph display key 46 that also acts as the fixed/automatic mode switch key functions to switch between the fixed mode and the automatic mode. In similar manner depressing the data selection key 48 that also acts as the data erase key functions to erase the previous measurement data. Finally depressing the memory key 41, 42, 43 or 44 once again terminates the mode switching operation.

In the embodiment disclosed herein the time interval during which the reference data is set is preset to five days and each of the setting modes will be described in more detail.

1. Fixed setting mode:

In this mode the measurement data acquired for the time interval of five days is used to calculate the reference data which is then kept fixed until the time it is to be re-set. The time interval of five days means that the non-volatile memory 5 stores the measurement data for five days. In particular when the apparatus of the present invention is put into operation for the first time it enters the fixed setting mode. Due to the fact that the non-volatile memory 5 has no data stored therein the time interval for acquiring the measurement data required for calculation of the reference data corresponds to the preset time interval of five days. Therefore, in the measurement operation for a first day, because of no data stored, the graph display is not activated. But the measurement data acquired each time is averaged and stored in the non-volatile memory 5 as the reference data.

If the mode switching operation as described above is used to switch to the fixed setting mode the operation of the apparatus varies depending on how much measurement data the non-volatile memory 5 has stored. If the non-volatile memory 5 stores the measurement data more than that for five days the reference data is calculated based on the measurement data for five days. However, if the non-volatile memory 5 stores only the measurement data less than that for four days, for instance, a temporary reference data is produced using that measurement data. After the measurement data for five days has been acquired the reference data is calculated based on such measurement data.

2. Automatic setting mode:

In this mode the reference data is automatically calculated and updated always using the latest measurement data for five days. If there is only the measurement data less than that for four days, for instance, a temporary reference data is produced. After the measurement data for five days has been acquired the reference data is calculated based on such measurement data.

Now the calculation of the degree of swelling will be described in more detail. The calculation of the degree of swelling is performed based on the personal data or the reference data as described above. The reference data used for calculation of the degree of swelling is set on the basis of the bioelectrical impedance as measured in each day's morning and the measurement time instance therefor; as well as the bioelectrical impedance as measured in each day's evening or night and the measurement time instance therefor.

In this embodiment the time interval during which the reference data is set is preset to five days, and the description of setting of the reference data will be made hereafter.

Initially an average value "Zam" for the bioelectrical impedance data as measured in each day's morning and an average time "Tam" for the measurement time instances at which the impedance measurements are made are calculated. In similar manner an average value "Zpm" for the bioelectrical impedance data as measured in each day's evening or night and an average time "Tpm" for the measurement time instances at which the impedance measurements are made are calculated.

$$Zam=\Sigma Zai/5 \ (i=1, 2, \ldots 5)$$

$$Zpm=\Sigma Zpi/5 \ (i=1, 2, \ldots 5)$$

$$Tam=\Sigma Tai/5 \ (i=1, 2, \ldots 5)$$

$$Tpm=\Sigma Tpi/5 \ (i=1, 2, \ldots 5)$$

Wherein "Zai" is a bioelectrical impedance value as measured in the morning of "i"th day; and "Tai" is a measurement time instance at which the impedance measurement is made. Similarly "Zpi" is a bioelectrical impedance value as measured in the evening or night of "i"th day; and "Tpi" is a measurement time instance at which the impedance measurement is made.

Then the difference "Zap" between the averages "Zam" and "Zpm" for the bioelectiical impedance values for the moining and for the evening or night is calculated.

$$Zap=Zam-Zpm$$

The difference "Zap" represents an average for a change in amount of interstitial fluid for a whole day for a person under test. Therefore comparison of this value "Zap" with the actual measurement data in every day makes possible to determine whether the change in amount of interstitial fluid is greater or lesser relative to the normal condition for the person. In other words the degree of welling for the person can be determined.

According to this embodiment the reference data is set by the difference "Zap" between the averages "Zam" and "Zpm" for the bioelectrical impedance values for the morning and for the evening or night; and the average time "Tam" and "Tpm" for the measurement time instances at which the measurements are made.

Based on such reference data, the degree of swelling is calculated from the bioelectrical impedance values as measured in the morning and in the evening or night in the following manner:

Assuming that the bioelectrical impedance value as measured in the morning is "Z1", then the degree of swelling in the morning "M1" is expressed by the following formula:

$$M1=(Z1-Zam)/Zap$$

This determines whether the degree of swelling as measured in the morning is higher or lower as compared to the reference. If "M1" has a positive value the degree of swelling is higher than the reference. However if it has a negative value the degree of swelling is lower than the reference.

Assuming that the bioelectrical impedance value as measured in the evening or night is "Z2", then the difference $\Delta Z$ between it and the impedance value in the morning "Z1" is calculated.

$$\Delta Z=Z1-Z2$$

This $\Delta Z$ represents a change in amount of interstitial fluid between those in the morning and in the evening or night, that is, the swelling for a whole day. Thus the degree of swelling for a whole day "M2" is expressed by the following formula:

$$M2=(\Delta Z-Zap)/Zap$$

If "M2" has a positive value the degree of swelling is higher than the reference. However if it has a negative value the degree of swelling is lower than the reference.

In such manner the calculation of the degree of swelling according to the embodiment is performed on the basis of an averaged value for the swelling in the normal life that is used as the reference.

The data "Tam" and "Tpm" are used for determining whether the measurement is performed in the morning or in the evening or night by comparing such data with the time instance at which the person performs the measurement.

Now reference will be made to another embodiment of the present invention in which a temporal swelling occurred on a person is measured. This applies to such case that when the person feels a fatigue the person massages his own lower limbs or takes a bath to relieve the fatigue. By performing the measurement before and after such massaging or taking a bath, it is possible to determine whether the fatigue is relieved or not by comparing the degree of swelling before and after such action.

Figure 13:
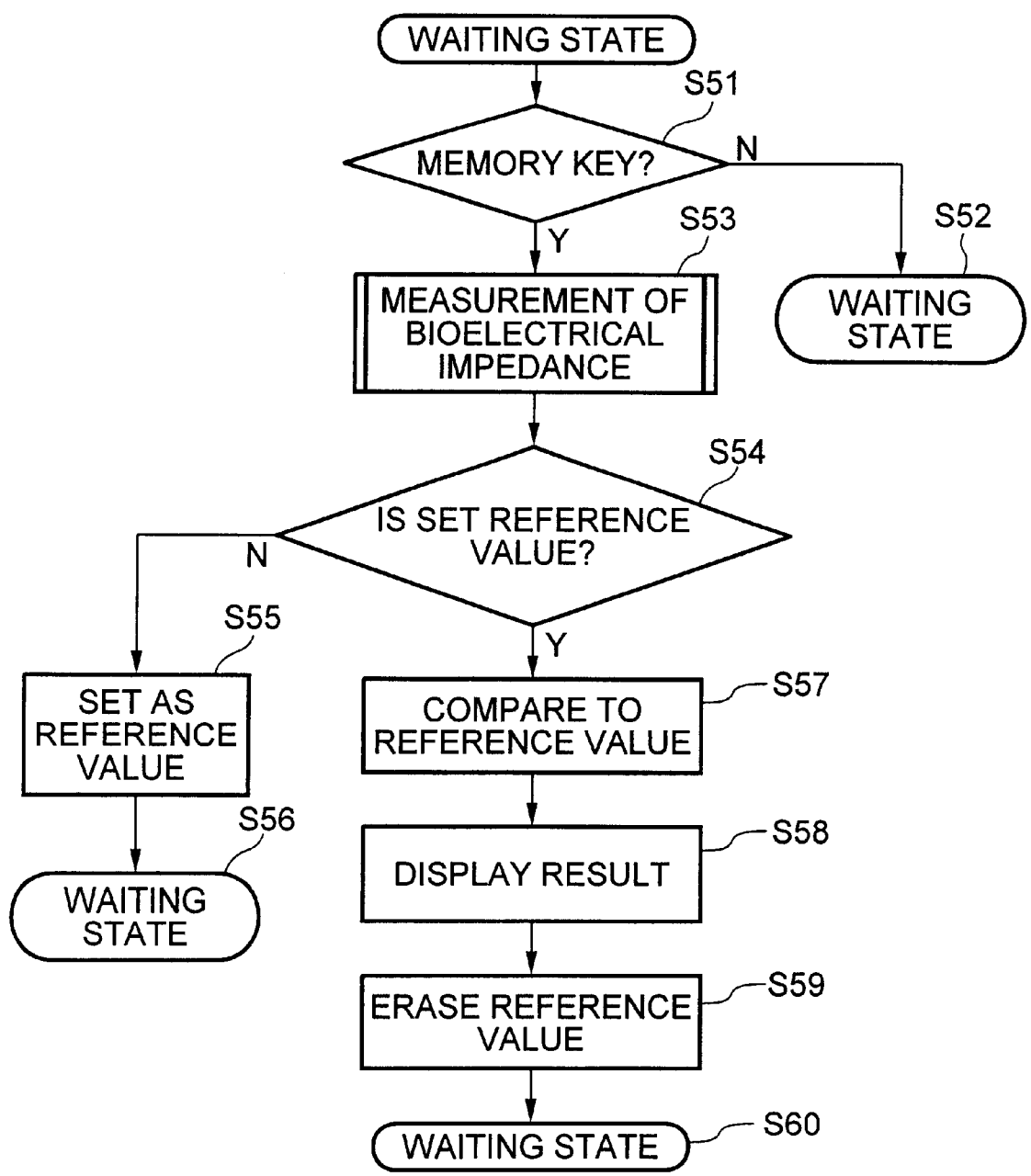
FIG. 13 is a flow chart illustrating measurement steps according to further embodiment of the present invention.

Description of this second embodiment will be made with reference to a flow chart in FIG. 13. The external overview and the internal components of the second embodiment are same as those in FIGS. 5 and 6, respectively.

After a waiting condition, a check is made to see whether any one of the memory keys 41, 42, 43 and 44 is depressed (step S51). If not, the procedure does not enter an operation mode, but keeps in the waiting condition (step S52).

However if any one of the memory keys 41, 42, 43 and 44 is depressed in step S51 the measurement of the bioelectrical impedance is performed (step S53). Then a check is made to see whether the data corresponding the key number of the memory key depressed is stored in the non-volatile memory 5 (step S54). If such data is not stored in the memory 5, then the measured value of bioelectrical impedance is taken as the reference (step S55) and the procedure enters the waiting mode (step S56). In general the reference value is set before an action such as massaging or taking a bath is performed. The subroutine for measuring the bioelectrical impedance is same as that shown in FIG. 10.

If the reference data is already stored in the memory in step S54 then it is compared with the measured value of the bioelectrical impedance to determine a change in degree of swelling before and after the action (step S57). In such determination, assuming that the reference value of impedance before the action is "Zp" and the impedance after the action is "Zn", the degree of swelling at that time "Mn" is expressed by the following formula:

$$Mn=(Zn-Zp)/Zp$$

This determines whether the degree of swelling after the action is higher or lower than that before the action. If "Mn" has a positive value it means that the degree of swelling after the action is higher than that before the action. But, if it has a negative value, the degree of swelling has been reduced after the action.

Then the degree of swelling as calculated is displayed (step S58), the reference value set before the action for use in the determination is erased (step S59), and the procedure enters the waiting mode (step S60).

According to the second embodiment as above a change in degree of swelling before and after the action such as massaging or taking a bath can be captured so that the person can see the effectiveness for massaging or taking a bath.

In the first embodiment as described earlier the description has been made as using the averaged change in amount of interstitial fluid as the reference data. However more simple case may be possible wherein the measurement of the bioelectrical impedance for the person under test is repeated several times in every morning and night in the normal life, and the average values thereof are stored as the reference. Then the presence of swelling can be determined simply by comparing the measured value of bioelectrical impedance with that reference. Alternatively the reference data may be set by the bioelectrical impedance measured only in the previous day, rather than by those measured over a several days. In such case the degree of swelling may be determined simply by comparing with the data in the previous day.

The method of calculating the degree of swelling for the person through the measurement of bioelectrical impedance has been described in the first embodiment as above. As described earlier, provided that the change in amount of interstitial fluid, extra-cellular water and body water in a part of the person under test can be obtained, the bioelectrical impedance measuring method may use either of a single frequency and multiple frequencies. In addition the numerical parameter used for the calculation may be any one of bioelectrical impedance, ratio of intra-cellular/extra-cellular water, and other parameters as derived from the bioelectrical impedance.

Figure 12:
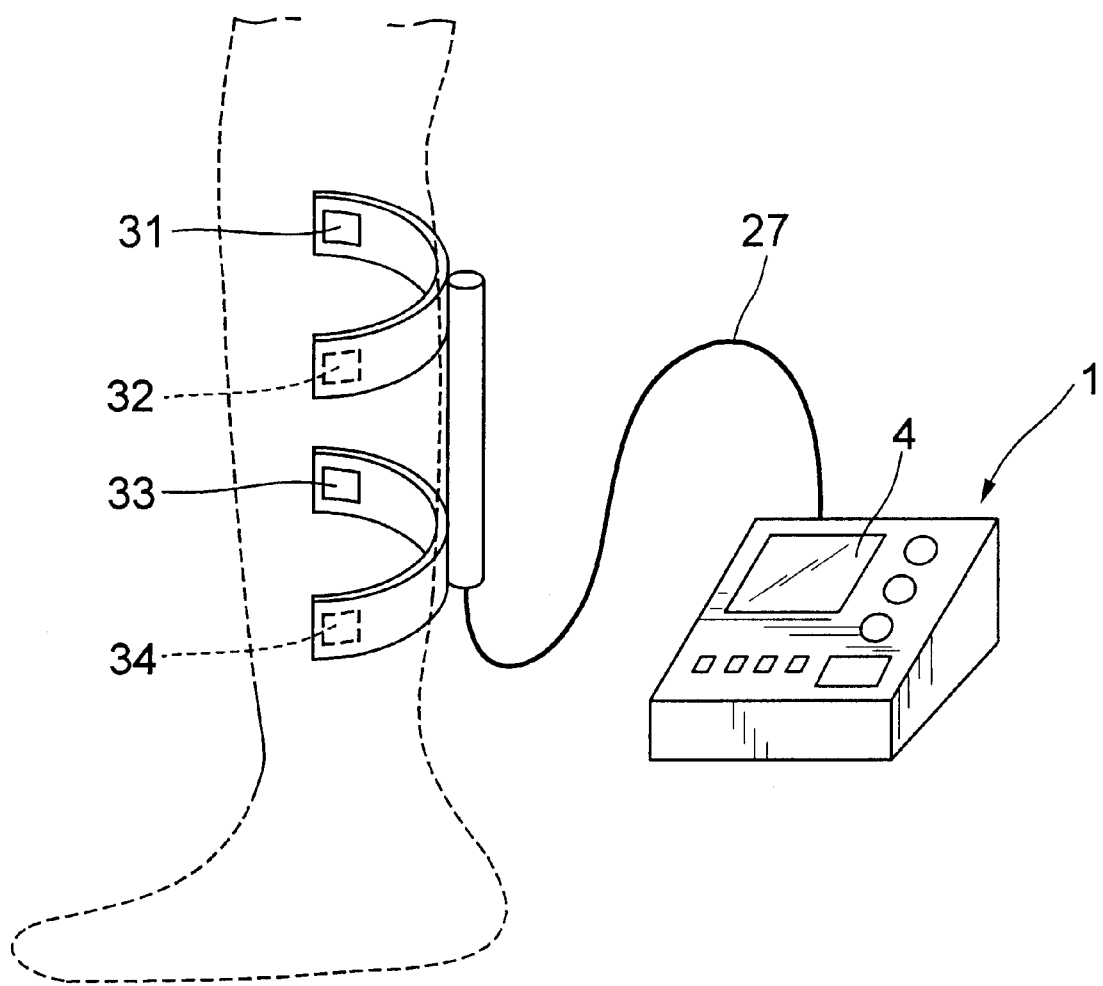
FIG. 12 is an overview illustrating another embodiment of the present invention.

The configuration of the electrodes wherein two pairs of electrodes of the apparatus are configured to contact with both soles of the person under test has been described in the first embodiment as above. However the present invention is not limited to such configuration of the electrodes and any other electrode configuration may be applied if it can measure the bioelectrical impedance on the lower limbs. FIG. 12 shows another electrode configuration in which two pairs of electrodes 31, 32 and 33, 34 are made directly contact with a calf of one leg. According to such electrode configuration the bioelectrical impedance can be measured substantially on the calf where the swelling is most likely be appeared. This enables reduction of any error factor as compared to other configuration, and therefore, more precise determination of the swelling becomes possible. In addition if the impedance including that for a foot is known it is possible to see the degree of swelling. Therefore the present invention is applicable to the case where the bioelectrical impedance between limbs or hands and legs is measured.

It is apparent from the foregoing that an apparatus for determining a degree of fatigue of a human body is operated to detect and store the degree of swelling as the measure of fatigue of the body through a bioelectrical impedance measurement method. Then the apparatus calculates a reference data used for determining the degree of swelling for the person on the basis of the stored data of the degree of swelling, and compares the current data of the degree of swelling with such reference to determine the degree of fatigue. Therefore it becomes possible to more precisely and objectively determine the degree of fatigue of the body according to the personal characteristic of each of the persons under test.

In addition it is possible to estimate a change in body condition and an accumulation of fatigue of the person based on the previous data for the degree of swelling.

When a multi-frequency AC current is used for the measurement current the degree of swelling can be determined on the basis of a ratio of intra-cellular/extra-cellular water. Thus it becomes possible to make the measurement independent of a change in bioelectrical impedance due to the body temperature.

Alternatively when a single-frequency AC current is used for the measurement current the apparatus can be realized with more simple circuit configuration, and shortening of measurement time can be attained.

What is claimed is:

1. An apparatus for determining a degree of fatigue of a human body, comprising:

two pairs of electrodes;

an electric current source;

a voltage measuring unit;

an arithmetic unit;

a storage unit; and a display unit, whereby said two pairs of electrodes are configured to contact with a body of a person under test;

said electric current source feeds a measurement current via selected ones of said electrodes;

said voltage measuring unit measures a voltage between another selected ones of said electrodes;

said storage unit stores a bioelectrical impedance or a parameter as derived from the bioelectrical impedance calculated by said arithmetic unit and a reference value of the bioelectrical impedance or the parameter as derived from the bioelectrical impedance;

said arithmetic unit calculates the bioelectrical impedance or a parameter as derived from the bioelectrical impedance based on the measurement value from said voltage measurement unit and then calculates a degree of fatigue of the person under test by comparing the currently measured value of the bioelectrical impedance or the parameter as derived from the bioelectrical impedance with the reference value of the bioelectrical impedance or the parameter as derived from the bioelectrical impedance stored in the storage unit; and said display unit indicates the degree of fatigue of the person under test.

2. An apparatus for determining a degree of fatigue according to claim 1 in which said display unit graphically indicates the transition of change in degree of fatigue.

3. An apparatus for determining a degree of fatigue according to claim 2 in which the graph displayed on said display unit represents the transition of change in degree of fatigue on the basis of the bioelectrical impedance as measured in the morning.

4. An apparatus for determining a degree of fatigue according to claim 2 in which the graph displayed on said display unit represents the transition of change in degree of fatigue on the basis of the bioelectrical impedance as measured in the evening or night.

5. An apparatus for determining a degree of fatigue according to claim 1 in which said reference value of bioelectrical impedance is set before a certain action is carried out by a person under test, and said display unit indicates the degree of fatigue before and after such action by comparing the currently measured value of the bioelectrical impedance with the reference value of the bioelectrical impedance stored in the storage unit.

6. An apparatus for determining a degree of fatigue based on the swelling of a human body, comprising:
   two pairs of electrodes;
   an electric current source;
   a voltage measuring unit;
   an arithmetic unit;
   a storage unit; and
   a display unit,
   whereby said two pairs of electrodes are configured to contact with a body of a person under test;
   said electric current source feeds a measurement current via selected ones of said electrodes;
   said voltage measuring unit measures a voltage between another selected ones of said electrodes;
   said storage unit stores a bioelectrical impedance or a parameter as derived from the bioelectrical impedance calculated by said arithmetic unit and a reference value of the bioelectrical impedance or a parameter as derived from the bioelectrical impedance;
   said arithmetic unit calculates the bioelectrical impedance or a parameter as derived from the bioelectrical impedance based on the measurement value of said voltage measurement unit and then calculates a degree of swelling of the person under test by comparing the currently measured value of the bioelectrical impedance or the parameter as derived from the bioelectrical impedance with the reference value of the bioelectrical impedance or the parameter as derived from the bioelectrical impedance stored in the storage unit; and
   said display unit indicates a degree of swelling of the person under test.

7. An apparatus for determining a degree of fatigue according to claim 6 in which said display unit graphically indicates the transition of change in degree of swelling.

8. An apparatus for determining a degree of fatigue according to claim 7 in which the graph displayed on said display unit represents the transition of change in degree of swelling on the basis of the bioelectrical impedance as measured in the morning.

9. An apparatus for determining a degree of fatigue according to claim 7 in which the graph displayed on said display unit represents the transition of change in degree of swelling on the basis of the bioelectrical impedance as measured in the evening or night.

10. An apparatus for determining a degree of fatigue according to claim 6 in which said reference value of bioelectrical impedance is set before a certain action is carried out by a person under test, and said display unit indicates the degree of swelling before and after such action by comparing the currently measured value of the bioelectrical impedance with the reference value of the bioelectrical impedance stored in the storage unit.

11. An apparatus for determining a degree of fatigue of according to claim 1 in which said reference value of the bioelectrical impedance represents an average change in amount of interstitial fluid that is the difference between average values for a plurality of measurements in every morning and in every night.

12. An apparatus for determining a degree of fatigue according to claim 11 in which said average change in amount of interstitial fluid is updated every time when the bioelectrical impedance is measured.

13. An apparatus for determining a degree of fatigue according to claim 1 in which said electric current source selectively feeds the measurement current having a plurality of frequencies.

14. An apparatus for determining a degree of fatigue according to claim 1 in which said electric current source feeds the measurement current having a single frequency.

15. An apparatus for determining a degree of fatigue according to claim 1 in which said two pairs of electrodes are configured to contact with both soles of the person under test.

16. An apparatus for determining a degree of fatigue according to claim 1 in which said two pairs of electrodes are configured to contact with a calf of the person under test.

17. An apparatus for determining a degree of fatigue of a human body, comprising:
   two pairs of electrodes;
   an electric current source;
   a voltage measuring unit;
   an arithmetic unit;
   a storage unit; and
   a display unit,
   whereby said two pairs of electrodes are configured to contact a body of a person under test;
   said electric current source feeds a measurement current via selected ones of said electrodes;
   said voltage measuring unit measures a voltage between other selected ones of said electrodes;
   said storage unit stores a bioelectrical impedance or a parameter as derived from the bioelectrical impedance calculated by said arithmetic unit and a reference value of the bioelectrical impedance or the parameter as derived from the bioelectrical impedance;
   said arithmetic unit calculates the bioelectrical impedance or a parameter as derived from the bioelectrical impedance based on the measurement value from said voltage measuring unit and then calculates a degree of fatigue of the person under test by comparing the currently measured value of the bioelectrical impedance or the parameter as derived from the bioelectrical impedance with the reference value of the bioelectrical impedance or the parameter as derived from the bioelectrical impedance stored in the storage unit; and
   said display unit graphically indicates the transition of change in degree of fatigue, said reference value being an average change in amount of interstitial fluid.

18. An apparatus for determining a degree of fatigue according to claim 17 in which the graph displayed on said display unit represents the transition of change in degree of fatigue on the basis of the bioelectrical impedance as measured in the morning.

19. An apparatus for determining a degree of fatigue according to claim 17 in which the graph displayed on said display unit represents the transition of change in degree of fatigue on the basis of the bioelectrical impedance as measured in the evening or night.

20. An apparatus for determining a degree of fatigue according to claim 17 in which said reference value of the bioelectrical impedance represents an average change in amount of interstitial fluid that is the difference between average values for a plurality of measurements in every morning and in every night.

21. An apparatus for determining a degree of fatigue according to claim 20 in which said average change in amount of interstitial fluid is undated every time when the bioelectrical impedance is measured.

22. An apparatus for determining a degree of fatigue based on the swelling of a human body, comprising:

two pairs of electrodes;

an electrical current source;

a voltage measuring unit;

an arithmetic unit;

a storage unit; and a display unit, whereby said two pairs of electrodes are configured to contact with a body of a person under test;

said electric current source feeds a measurement current via selected ones of said electrodes;

said voltage measuring unit measures a voltage between other selected ones of said electrodes;

said storage unit stores a bioelectrical impedance or a parameter as derived from the bioelectrical impedance calculated by said arithmetic unit and a reference value of the bioelectrical impedance or the parameter as derived from the bioelectrical impedance;

said arithmetic unit calculates the bioelectrical impedance or a parameter as derived from the bioelectrical impedance based on the measurement value from said voltage measuring unit and then calculates a degree of swelling of the person under test by comparing the currently measured value of the bioelectrical impedance or the parameter as derived from the bioelectrical impedance with the reference value of the bioelectrical impedance or the parameter as derived from the bioelectrical impedance stored in the storage unit; and said display unit graphically indicates the transition of change in degree of fatigue on the basis of swelling.

23. An apparatus for determining a degree of fatigue according to claim 22 in which the graph displayed on said display unit represents the transition of change in degree of swelling on the basis of the bioelectrical impedance as measured in the morning.

24. An apparatus for determining a degree of fatigue according to claim 22 in which the graph displayed on said display unit represents the transition of change in degree of swelling on the basis of the bioelectrical impedance as measured in the evening or night.

* * * * *